United States Patent [19]
Bessette et al.

[11] Patent Number: 6,114,384
[45] Date of Patent: *Sep. 5, 2000

[54] NON-HAZARDOUS PEST CONTROL

[75] Inventors: Steven M. Bessette; Arthur M. Knight, both of Alpharetta, Ga.

[73] Assignee: Ecosmart, Inc., Roswell, Ga.

[*] Notice: This patent is subject to a terminal disclaimer.

[21] Appl. No.: 08/657,585

[22] Filed: Jun. 7, 1996

Related U.S. Application Data

[63] Continuation-in-part of application No. PCT/US94/05823, May 20, 1994, and a continuation-in-part of application No. 08/553,475, Nov. 9, 1995, Pat. No. 5,693,344, which is a continuation-in-part of application No. 08/065,594, May 21, 1993, Pat. No. 5,439,690.

[51] Int. Cl.$^7$ .......................... A01N 37/02; A01N 31/14; A01N 31/04

[52] U.S. Cl. .......................... 514/546; 514/720; 514/730; 514/875

[58] Field of Search .................... 514/718, 720, 514/733, 546, 730

[56] References Cited

U.S. PATENT DOCUMENTS

| | | | |
|---|---|---|---|
| 4,368,207 | 1/1983 | Lover et al. | 514/724 |
| 4,721,727 | 1/1988 | Mikolajczak et al. | 514/473 |
| 5,990,157 | 11/1999 | Zocchi et al. | 514/464 |
| 6,001,874 | 12/1999 | Veierov | 514/533 |
| 6,004,569 | 12/1999 | Bessette et al. | 424/406 |

FOREIGN PATENT DOCUMENTS

| | | |
|---|---|---|
| 3901341 | 7/1990 | Germany. |
| 4231045 | 3/1994 | Germany. |
| 3264504 | 11/1991 | Japan. |

OTHER PUBLICATIONS

Chemical Abstracts 131:307910j, abstracting WO 99/56538 (Nov. 11, 1999).

Tsao et al, "Synthesis and Chemistry of Agrochemicals IV", Chapter 28, pp. 312–324 (1995), ACS Symposium Series 584.

Rice and Coats, "Bioregulators for Crop Protection and Pest Control", Chapter 8, pp. 92–108 (1994), ACS Symposium Series 557.

Wilkinson, editor, "Insecticide Biochemistry and Physiology", Plenum Press, New York, 1976, pp. 438–440.

Dev and Koul, "Insecticides of Natural Origin", Harwood Academic Publishers, Amsterdam 1997, pp. vii, viii, and 5 and 47–58.

Metcalf and McKelvey, Jr., editors, "The Future for Insecticides, Needs and Propects", Wiley–Interscience, New York, 1976, pp. 97–113.

Merck Index, 11$^{th}$ Edition, pp. 176, 612–613 and 1146–1147 (1989).

Hollingworth, R.M. 1976. The biochemical and physiological basis of selective toxicity. In: *Insecticide Biochemistry and Physiology*, C.F. Wilkinson (ed.), Plenum Press, New York, pp. 431–506.

Escoubas, P., L. Lajide and J. Mizutani. Insecticidal and antifeedant activities of plant compounds. Potential leads for novel pesticides. In: *Natural and Engineered Pest Management Agents*, P.A. Hedin, J.J. Menn and R.M. Hollingworth (eds.), American Chemical Society Symposium Series 551:162–171, 1994.

Fields, P.G. et al. 1991. Phototoxins as insecticides and natural plant defenses. *Mem. Entomol. Soc. Canada* 159:29–38.

Lowery, D.T. and M.B. Isman. 1994. Insect growth regulating effects of neem extract and azadirachtin on aphids. *Entomol. Exp. Appl.* 72:77–84.

Marcus, C. and E.P. Lichtenstein. 1979. Biologically active components of anise: toxicity and interactions with insecticides in insects. *J. Agric. Food Chem.* 27:1217–1223.

Mitsui, T. et al. 1991. Search for insect growth regulators. *Rev. Pestic. Toxicol.* 1:239–247.

Chemical Abstracts 114:116930, 1991.

Chemical Abstracts 84:55270, 1974.

Derwent Abstract, Accession No. 1994–102240, 1994.

King, W.V., Chemicals Evaluated as Insecticides and Repellents at Orlando, Fla., AGricultural Handbook No. 69, U.S. Dept. of Agriculture, 1954, pp. 1–19, 26, 174 and 255.

Chemical Abstracts 116: 123317 (1992).

Deshpande et al., "Stored Grain Pest Control Agents from *Nigella sativa* and *Pogostemon heyneanus*," Bull. Grain Technol., vol. 12(3), 1974, pp. 232–234.

*Primary Examiner*—John Pak
*Attorney, Agent, or Firm*—Leonard Bloom

[57] ABSTRACT

A method for controlling insects and arachnids using a composition which is non-toxic to humans. The composition may be a dust, an aerosol or a solvent solution of at least one neurally effective substance. The neurally effective substance has the following general chemical structure,

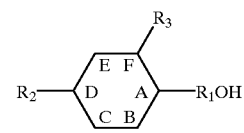

where $R_1$ is any of the following:
$CH_2$, $C_2H_4$, $C_3H_6$, $C_3H_4$, $C_4H_8$ or $C_4H_4$;
where $R_2$ is any of the following:
H, $H_2$, $CH_3$, $C_2H_5$, $C_3H_7$, $C_3H_5$, $C_4H_9$ or $C_4H_5$;
where $R_3$ is any of the following:
H, $H_2$ or $OCH_3$;

where the six member ring ABCDEF has at least one unsaturated bond therein. The neurally active substances may also be an ester of the hydroxyl group on $R_1$. Specific active compounds encompass terpineol, phenylethyl alcohol, benzylacetate, benzyl alcohol, eugenol, cinnamic alcohol and mixtures thereof.

5 Claims, No Drawings

NON-HAZARDOUS PEST CONTROL

CROSS REFERENCE TO RELATED APPLICATIONS

The present application is a continuation-in-part of pending application Ser. No. PCT/US94/05823, filed May 20, 1994, and the U.S. national phase Ser. No. 08/553,475, filed Nov. 9, 1995, now U.S. Pat. No. 5,693,344, which is, in turn, a continuation-in-part of U.S. patent application Ser. No. 08/065,594 filed May 21, 1993 which has subsequently issued as U.S. Pat. No. 5,439,690, issued Aug. 8, 1995.

BACKGROUND OF THE INVENTION

The present invention relates to the control of pests such as insects and arachnids and, more particularly, to a non-hazardous pest control agent that eliminates pests through either neural effects of a component or mechanical puncture of the exoskeleton and also, through the neurally effective component entering the puncture.

Insects and other pests have long plagued humankind. Over the years, various approaches have been taken to control pests and especially insects, and none have been completely satisfactory.

For example, the use of complex, organic insecticides, such as disclosed in U.S. Pat. Nos. 4,376,784 and 4,308,279, are expensive to produce, can be hazardous to man, domestic animals, and the environment, and frequently are effective only on certain groups of insects. Moreover, the target insects often build an immunity to the insecticide.

Another approach employs absorbent organic polymers for widespread dehydration of the insects. See, U.S. Pat. Nos. 4,985,251; 4,983,390; 4,818,534; and 4,983,389. However, this approach is limited predominantly to aquatic environments, and it likewise relies on hazardous chemical insecticidal agents. Further, the addition of essential oils is primarily as an insect attractant.

In addition, this approach is based on the selective absorption of a thin layer of insect wax from the exoskeleton and not to a puncture of the exoskeleton. [Sci. Pharm. Proc. 25th, Melchor et al, pp. 589–597 (1966)]

The use of inorganic salts as components of pesticides is reported by U.S. Pat. Nos. 2,423,284 and 4,948,013, European Patent Application No. 462 347, Chemical Abstracts 119(5):43357q (1993) and Farm Chemicals Handbook, page c102 (1987). These references disclose the inclusion of these components but not the puncturing of the exoskeleton of the insect by the salts.

The applicants are also aware of the following which disclose pesticides and insecticides: U.S. Pat. Nos. 4,806,526, 4,834,977, 5,110,594, 5,271,947 and 5,342,630.

The marketplace is replete with toxic chemical insecticidal agents that are offensive to apply and, more importantly, pose a danger to humans and the environment.

It would be greatly advantageous to solve these problems with a pesticidal agent that works neurally and with a penetrating substance to kill pests, thereby eliminating the need for any chemicals which are toxic to humans and domestic animals.

BRIEF SUMMARY OF THE INVENTION

Accordingly, it is an object of the invention to provide a method for non-hazardous pest control and a composition for the same which kills pests neurally and both mechanically and neurally.

It is another object to provide a safe, non-toxic pest control agent that will not harm the environment.

It is another object to provide a pest control agent that is highly effective in combating a wide variety of pests, including all insects and arachnids having an exoskeleton.

It is another object to provide a pest control agent which has either no scent or a pleasant scent, and which can be applied without burdensome safety precautions for humans and domestic animals.

It is still another object to provide a pest control agent as described above which can be inexpensively produced.

It is yet another object of the invention to provide a pest control agent to which pests cannot build an immunity.

In accordance with the above-described and other objects, the present invention provides a pesticide for insects and arachnids comprising a carrier and at least a neurally effective substance. The neurally effective substance has a chemical structure of $$R_2-\underset{C\ B}{\overset{E\ F}{\underset{D\quad A}{\bigcirc}}}-R_1OH$$

$$R_3$$

where $R_1$ is any of the following:
$CH_2$, $C_2H_4$, $C_3H_6$, $C_3H_4$, $C_4H_8$ or $C_4H_4$ where $R_2$ is any of the following:
H, $H_2$, $CH_3$, $C_2H_5$, $C_3H_7$, $C_3H_5$, $C_4H_9$ or $C_4H_5$ where $R_3$ is any of the following:
H, $H_2$ or $OCH_3$ where the six member ring ABCDEF has at least one unsaturated bond therein.

During the course of developing improved insecticidal compositions the inventors have found that various organic compounds when applied in a novel manner will unexpectedly act as a pesticide to kill insects and arachnids. Among the preferred compounds that applicants have found to be insecticidal are terpeniol, phenylethyl alcohol, benzyl acetate, benzyl alcohol, eugenol and cinnamic alcohol. To be affective these compounds should be incorporated into carriers preferably in the form of aerosols, dusts, solutions, liquid emulsions and the like.

The herein disclosed invention envisions a pesticide for insects and arachnids comprising a carrier and an effective amount of at least one neurally effective substance. In a specific embodiment the carrier is crystalline dust having a size effective to puncture the exoskeleton and to permit the neurally effective substance to enter the punctured exoskeleton and interfere with the bodily function of the insects and arachnids. Specifically the carrier can be a crystalline powder of a mixture of alkali metal bicarbonate, calcium carbonate, diatomaceous earth and amorphous silica. The crystalline powder has a particle size of 0.1 to 200 microns, and preferably under 100 microns, and the calcium carbonate can be in the form of ground pottery glaze. In an alternative embodiment the carrier is an aerosol spray having a solvent and a propellant, and is compatible and non-reactive with the neurally effective substance. Specifically the solvent can be an organic solvent, either aromatic or aliphatic, and wherein the propellant is carbon dioxide or dimethyl ether. It is to be understood that the solvent is compatible and nonreactive with the neurally effective substances. The neurally effective substances in the composition can be in the range of approximately 0.01% to 10% by weight of the pesticide composition. In some embodiments of the pesticidal composition the neurally effective substance is a mixture of two or more neurally effective substances and/or other diluents included for aesthetic purposes.

In an alternative embodiment of the pesticide for controlling insects and arachnids the composition comprises an effective amount of crystalline powder including calcium carbonate, alkali metal bicarbonate, absorbent material and at least one neurally effective substance having a chemical structure represented by the formula

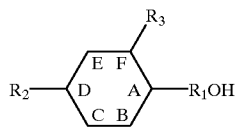

where $R_1$ is any of the following:
  $CH_2$, $C_2H_4$, $C_3H_6$, $C_3H_4$, $C_4H_8$ or $C_4H_4$
where $R_2$ is any of the following:
  H, $H_2$, $CH_3$, $C_2H_5$, $C_3H_7$, $C_3H_5$, $C_4H_9$ or $C_4H_5$
where $R_3$ is any of the following:
  H, $H_2$ or $OCH_3$, and
where the six member ring ABCDEF has at least one unsaturated bond therein, and also an ester of the hydroxyl group on $R_1$ when $R_1$ is $CH_2$, $R_2$ is H and $R_3$ is H, and specifically an acetate ester. The pesticide formulation contains the neurally effective substance in 0.1% to 10% by weight of the pesticide. The crystalline powder of this composition comprises calcium carbonate 27%–35%, sodium bicarbonate 54%–65% and absorbent material 4%–5% by weight.

In a particularly elegant embodiment of this invention the pesticide for controlling insects and arachnids comprises an aerosol spray including a solvent, a propellant and an effective amount of at least one neurally effective substance having a chemical structure of

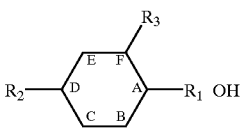

where $R_1$ is any of the following:
  $CH_2$, $C_2H_4$, $C_3H_6$, $C_3H_4$, $C_4H_8$ or $C_4H_4$
where $R_2$ is any of the following:
  H, $H_2$, $CH_3$, $C_2H_5$, $C_3H_7$, $C_3H_5$, $C_4H_9$ or $C_4H_5$
where $R_3$ is any of the following:
  H, $H_2$ or $OCH_3$, and
where the six member ring ABCDEF has at least one unsaturated bond therein, and wherein neurally effective substance can be an ester of the hydroxyl group on $R_1$ when $R_1$ is $CH_2$, $R_2$ is H and $R_3$ is H. Specifically the ester is an acetate ester. The neurally effective substance is present in 0.1% to 10% by weight of the pesticide. The propellant can be carbon dioxide. The solvent can be an organic solvent. The pesticide for insects and arachnids can contain a solvent and at least one neurally effective substance. The neurally effective substance can be 0.1% to 10% by weight of the pesticide. In preferred embodiments the compositions are an insecticidal aerosol formulation comprising as the active ingredient a member of the group consisting of terpineol, phenyl ethyl alcohol, benzyl acetate, benzyl alcohol, eugenol, cinnamic alcohol and mixtures thereof contained in an aerosol container including a propellant and a solvent.

These and other objects of the present invention will become apparent from a reading of the following specification.

DESCRIPTION

Most insects have an exoskeleton, cuticle or outer shell which has an outer waxy coating. There are microscopic wax canals in the cuticle. The exoskeleton typically comprises multiple body plates joined together by cartilaginous membrane.

This thin shell and the waxy coating is the primary protection the insect has to insure the maintenance of its vital body fluids. If an insect loses as little as 10% of these fluids, it will die.

The exoskeleton provides protection against most foreign agents such as pesticidal liquids and powders. For this reason, ingestion is the primary method of delivery for conventional pesticides and may also be a method of delivery of the pesticide of the present invention. However, pests will only ingest certain substances and in small amounts. This imposes limits on the types of usable pesticides and their effectiveness. For instance, insects generally will not ingest fatal amounts of dehydrating pesticide.

The present invention proposes new methods of delivery of a pesticide for insects and arachnids. The pesticide is at least one neurally effective chemical having a functional hydroxyl group in the proximity of a six member carbon ring. The neurally effective chemical, it is believed, is capable of dissolving or in some manner, penetrating the cuticle or waxy coated exoskeleton such that the hydroxyl group of the chemical interacts or binds with a vital substance within the insect or arachnid. This binding is fatal to the insect or arachnid. The neurally effective chemical is dispersed in a carrier which may be a dust, aerosol, emulsion or solvent carrier. The aerosol carrier and the liquid carrier provide an effective media to expose the insect or arachnid to the neurally effective chemical. The dust media provides a carrier to mechanically puncture the exoskeleton and accelerate the interaction between the neurally active chemical and the vital substance within the insect or arachnid. The dust media also is a dehydrating agent which provides another mode for killing the insect or arachnid.

A dust media containing diatomaceous earth, sodium bicarbonate, calcium carbonate and amorphous silica affect most insects very slowly, usually over several hours. Symptomology of exposure to these dusts is a gradual reduction in activity, slow loss of weight, and eventual death. These dusts do not provide rapid or sudden "knockdown".

Diatomaceous earth is a mild abrasive and desiccant. It abrades the cuticle and adsorbs the outer epicuticlar wax layer of several kinds of insects. Some, but not all, insects that lose the protective wax layer under dry conditions succumb within hours from evaporative loss of body water through the remaining integument. Unaffected insects may have a protective basal cement layer in the cuticle that affords additional protection from desiccation. Because some insects may replace surface wax quickly, a mild desiccant such as diatomaceous earth is not effective when the air is moist and has little evaporative power. Even when effective against insects, diatomaceous earth works fairly slowly.

A synergistic effect of calcium carbonate and calcium carbonate with other ingredients is possible, but unlikely. Rapid knockdown or paralysis of insects exposed to heavy deposits of either of these dusts has not been observed.

By their physical nature, several kinds of lightweight dusts with small pore size (i.e. very small particle size) that are not ordinarily considered desiccants may adsorb insect wax, in a similar fashion to diatomaceous earth. Adsorption eventually leads to lethal desiccation if the insect cannot replace the lost cuticular wax.

The rapid knockdown observed with the dust embodiment of the present pesticide is probably the result of an interaction between one or more of the dusts and a nerve-active substance, rather than from desiccation per se. The neurally effective substance may be the nerve-active substance. Once deposited on an insect, some dusts create a "water continuum" between the inside and outside of the insect. Hemolymph, in the form of lipid-water liquid crystals, is drawn by the dust to the surface from the interior of the insect through microscopic wax canals in the cuticle. Substances carried in the dust may then pass through the continuum into the insect where they come in contact with nerves bathed by the hemolymph. This process may occur very rapidly.

Another possibility of action is that the dust components facilitate rapid penetration of an active substance through the cuticle. Oily and alcoholic substances such as the neurally effective substance reported herein may readily penetrate thin or untanned portions of cuticle. The dusts may act as a dust diluent for a more "active" compound. Non-sorptive dusts such as diatomaceous earth tend to be effective diluents because they do not bind substances too tightly, thereby making the substance they carry available to the insect surface. Nerves near spiracles or other sensitive sites may be quickly affected, and may result in rapid knockdown, paralysis or death.

Bear in mind that the dust composition of this application, unlike previous dust compositions do not have to be boiled or cooked.

The following substances have been found to be active ingredients, useful as neurally effective substances:
  benzyl alcohol
  benzyl acetate
  phenyl ethyl alcohol
  terpineol
  cinnamic alcohol
  phenol
  eugenol.

The neurally active substances have the general structural formula $$R_2-\underset{C\ B}{\overset{E\ F}{\underset{D\ A}{\bigcirc}}}-R_1OH$$
$$\overset{R_3}{|}$$

where $R_1$ is any of the following:
  $CH_2$, $C_2H_4$, $C_3H_6$, $C_3H_4$, $C_4H_8$ or $C_4H_4$
where $R_2$ is any of the following:
  H, $H_2$, $CH_3$, $C_2H_5$, $C_3H_7$, $C_3H_5$, $C_4H_9$ or $C_4H_5$
where $R_3$ is any of the following:
  H, $H_2$ or $OCH_3$
where the six member ring ABCDEF has at least one unsaturated bond therein.

The neurally active substances may also be an ester of the hydroxyl group on $R_1$.

Mixtures of several neurally effective substances have been found to be effective.

The effective concentration of the active ingredient will generally be in the range of 0.01% to 10% and will be the primary active ingredient or function as a synergist. It is to be understood that various known active synergists can be added to the disclosed compositions of this invention to enhance the insecticidal activity of the composition.

The compositions encompassed by this invention will find application for indoor application as well as outdoor application. The composition can be formulated as a "pet cologne" for application to pets. An odorless composition is contemplated; as well as compositions formulated to avoid allergic reactions. The floral fragrances contemplated by this invention are limitless.

None of the individual components are identified by the United States Environmental Protection Agency as having active insecticidal properties. All are considered to be inert in and of themselves at the concentration disclosed herein. Thus, the demonstration of toxic effects on pests is considered to be unexpected.

Applicants do not wish to be bound to the theory of neural activity.

If the pesticide of the present invention is liberally administered in the vicinity of the insects, it cannot be avoided by the insects and death is imminent. Moreover, it is impossible for the insects to build an immunity to the composition.

The powder (or dust) embodiment is prepared by processing and/or mixing the crystalline solids [alkali metal bicarbonate (54%–65%), calcium carbonate (27%–35%), amorphous silica (1%–3%) and diatomaceous earth (4%–5%)] in a ribbon blender for approximately five to fifteen minutes to obtain a particle size of approximately 1–100 microns and the neurally effective substance (or substances) is then intimately mixed with the blend of crystalline solids. The amorphous silica known as HiSil(R) 233 marketed by Harwick, Akron, Ohio has been used satisfactorily.

The aerosol embodiment is prepared by mixing the active neurally effective substance or substances (1%–7%) with a solvent such as a mixture of paraffin hydrocarbons (50%–95%). Isoparaffinic hydrocarbons sold by Exxon Corporation known as Isopar H, Isopar L and Isopar M have been used satisfactorily but the solvent is not limited to these products. The mix is introduced into an aerosol container together with a propellant such as carbon dioxide, dimethyl ether, propane or a propane-butane mixture (5%–18%). All proportions are by weight.

The liquid formulation or solvent embodiment is prepared by mixing the active neurally effective substance or substances (1%–5%) with the isoparaffin hydrocarbon solvent (75%–99%) and placing the mix into a container which can be used for dispensing the liquid.

EXAMPLES

The following formulations are typical of the aerosols which can be employed with the active ingredients of this invention.

The active ingredient included in the formulations herein consists of a neurally effective substance, a combination of neurally effective substances, or a combination of neurally effective substances and other diluents added for aesthetic purposes. It has been found that synergistic effects are produced with various combinations.

1. 3% active ingredient
   20% DME (Dimethyl ether)
   1.5% Propanol
   75.5% Isopar M
2. 1.5% active ingredient 20.0% DME (Dimethyl ether)
1.5% Propanol
77.0% Isopar M
3. 3.0% active ingredient
   3.5% $CO_2$ (Carbon dioxide)
   1.5% Propanol
   92.0% Isopar M
4. 1.5% active ingredient
   3.5% $CO_2$ (Carbon dioxide)
   1.5% Propanol
   93.5% Isopar M
5. Active ingredient: 1–7% by weight
   Solvent A: 50–94.1% by weight
   (any of the following)
     (a) Isopar H
     (b) Isopar L
     (c) Isopar M
   Solvent B: 0–10% by weight
   (any of the following)
     (a) d Limonene
     (b) Synthetic Solvents EE-195
     (c) Synthetic Solvents EE-216
     (d) Synthetic Solvents EE-235
   Propellant: 4.9%–18% by weight
     (a) Carbon dioxide
     (b) Propane
     (c) Propane-butane mixture The solvents and propellants may be any of the listed materials and/or combinations thereof and are not limited to those identified above. The materials identified have been found to be satisfactory.

$CO_2$ (carbon dioxide) and DME (dimethyl ether) are the preferred propellants used in the aerosol formulations, however other propellants known to those skilled in the art would be operative.

Propanol is used to make the active ingredient miscible with the Isopar M. Isopar M is not considered by EPA or the state of California as a VOC (volatile organic compound).

A typical liquid formulation is as follows: liquid formulation

Active insecticide: 1–5% by weight
Solvent A: 75–99% by weight
  (a) Isopar H
  (b) Isopar L
  (c) Isopar M
Solvent B: 0–20% by weight
  (a) d Limonene
  (b) Synthetic Solvents EE-195
  (c) Synthetic Solvents EE-216
  (d) Synthetic Solvents EE-235
Solvent C: 75–99% by weight
  (a) Soltrol 100

It is to be understood that the percentages set forth herein are approximations and can be varied within degrees by those skilled in the art and still attain effective results. Also, other substances may be used. The above-identified materials have been used satisfactorily. Soltrol 100 is a solvent of isoparaffinic hydrocarbons ($C_9$ through $C_{11}$) sold by Philips Chemical Co. The solvents listed may be used individually or in any combination.

A fragrance may be added if desired to enhance the marketing of the pesticide, especially for indoor use and for general retail markets. The pesticide may be used domestically, commercially, indoors, outdoors, for pets, nurseries, and agriculturally. The pesticide of the present invention has also been found to be useful for control of head lice on humans and as a repellent to be used on the skin of humans.

The resulting aerosol or liquid solvent formulations of the invention are compositions capable of directly invading the exoskeleton of most insects and arachnids. There are over one million species of common pests such as ants, roaches, fleas, termites, beetles, mites and spiders. All are potential targets.

Emulsifiable concentrate formulations are within the preview of this invention. These emulsifiable concentrates are particularly useful for outdoor application to plant foliage. These emulsifiable concentrates are easy to use; simply mix with water in the proper proportions and spray with conventional spray applicators. Emulsifiers and surfactants well known in the art can be used in preparing the emulsions which can penetrate plant material to aid in producing systemic action.

A study was conducted to determine the insecticidal activity of the present invention against commonly found insects such as German cockroaches, cat fleas and Argentine ants. As described the term "dust" is used for the insecticide in a dry crystalline powder form and the term "powder" is used for dry formulations that are intended to be mixed with water.

Tests With Cockroaches

Continuous exposure tests. The intrinsic insecticidal activity of the insecticide dust against *B. germanica* was determined by exposing cockroaches to fresh and aged deposits of the dust. Replicated groups of three to ten adult cockroaches from culture were confined to deposits of the dust, and its speed of action in terms of knockdown (KD) and paralysis was determined. Adult male cockroaches from culture were placed directly onto fairly heavy deposits of dust (1 to 1.2 cc) spread evenly on filter paper in covered 9-cm-diameter petri dishes. The time for irreversible KD to occur (KT) was determined from periodic, irregular observation. The insects were considered KD when they were on their back, or could be turned over, and could not right themselves within at least two minutes. KT-50 and KT-90 values (time for 50% and 90% KD, respectively) were calculated by interpolation of KD between times when data was collected; average KT value were obtained from the individual KD data. Comparison of KD activity was made with some commercial dust formulations including a non-fluorinated silica aerogel (SG-68), Drione™ (a fluorinated silica aerogel+pyrethrins), and a commercial diatomaceous earth (Celite™) applied and tested in the same manner.

The effects of atmospheric moisture and deposit age on the efficacy of the present insecticide dust were determined by the speed of action (KT) on cockroaches confined to deposits of the dust aged and tested at 98% (high) and 58% (moderate) relative humidity (RH). Average KT values were determined for fresh dust and for dust aged 2 weeks and 4 weeks. Cockroaches were exposed to 1 cc of dust in petri dishes, as described previously. Eighteen-mesh window screen covers on the dishes allowed for maintenance of the proper humidity and kept cockroaches from escaping from the damp dusts. For these tests dishes of dust were aged and tested on a wire mesh platform in saran-sealed aquaria. Enough dishes were prepared so that each deposit was tested only once. Water below the platform was used to maintain 98%RH, and a saturated aqueous sodium bromide solution was used to maintain 58% RH.

Choice box tests. The activity and repellency of the present insecticide dust in a choice test was determined with standard two-compartment choice boxes.

Choice boxes are 30.5 cm square, 10 cm tall wooden boxes, with a tempered masonite floor. A vertical partition panel separates the box into two equal-sized compartments.

A 1.3 cm hole at the top center of the partition panel allows cockroaches to move from one compartment to the other. Transparent sheet plexiglass (0.3 cm thick) taped to the top retains cockroaches in the box and allows observation of live and dead in each compartment. A piece of masonite keeps one compartment dark (dark compartment). The other compartment (light compartment) is exposed to normal room light conditions.

Five boxes were used for each treatment and the untreated control. For these tests 10 cc of test dust was spread evenly over the floor of the dark compartment and 20 adult male *B. germanica* were released into the light compartment, where there was food and water. A cork in the partition hole was removed two hours later, when the cockroaches settled. Cockroaches prefer to aggregate in the dark, and they will normally readily move from the light compartment to the dark compartment of untreated choice boxes within a day or two. Once the partition cork was removed, the insects could move from the light compartment into treated dark compartment. The number dead and alive in each compartment of each box was recorded every few days. It was presumed that mortality was produced by contact with the insecticide in the dark, regardless of where the insects eventually died. Reluctance to move into the dark is attributable to the repellency of the treatment. Repellent treatments usually result in increased survivorship in the light compartment.

The mortality produced in choice boxes, and the position of cockroaches in relation to the treatment, provides a measure of the likely ultimate efficacy of a treatment when used under actual field conditions. In choice box tests, cockroaches are given an opportunity to encounter or avoid insecticide deposits. Highly toxic deposits may be ineffectual if cockroaches sense their presence and avoid lethal contact with them. On the other hand, slow-acting insecticides such as boric acid are effective in choice box tests because cockroaches readily walk on those deposits and are eventually killed by them.

Tests With Cat Fleas

Adult cat fleas, cultured under laboratory conditions were used in the study. Eggs collected from caged cats were reared through the larval period to adulthood on a special blood media. Adults used in the tests were approximately 2 to 3 days old (i.e., 2 to 3 days post-eclosion from the cocoon stage).

Speed of action of minimal deposits. The rate of knockdown of fleas exposed to filter paper treated with the present insecticide dust and SG-68 silica aerogel was determined. Strips of No. 1 Whatman filter paper measuring 2 cm by 15 cm were submerged in the dusts and the excess shaken off. The lightly dusted strips were slipped into 2.5 cm-diameter by 15 cm tall glass test tubes and groups of fleas were directed from rearing emergence jars into the tubes. The open end of the tube was covered with parafilm. The tubes were left in a vertical position in a test tube rack. Because such a small amount of dust was used, all of it adhered to the paper and none could be seen on the surface of the test tubes. The fleas contacted the dust when they walked on the paper. Exposure to the dust was ensured because live fleas prefer the paper surface to the smooth surface of the test tube. Knockdown of fleas in the tubes was observed and recorded every few minutes until all the fleas were down. The fleas were considered KD if they were paralyzed at the bottom of the tube. Rate of KD (KT) was interpolated from the number of fleas KD at each time of observation.

Exposures on dusted carpet. The minimum lethal dose and potential effectiveness of the present insecticide dust against fleas indoors was determined by exposing aliquots of fleas to a series of decreasing dosages of the dust on carpet. Dri-Die™ SG-68, a sorptive desiccant silica aerogel, was used as a comparative standard.

Weighed amounts of dust were sifted as evenly as possible onto the surface of 9-cm-diameter disks of new shag carpet at the bottom of 9 cm by 45-cm-tall plastic cylinders. The carpet was made of 100% nylon fibers and a jute backing. It has 9 double-stranded loops per $cm^2$, each strand being about 1.6 cm long.

The highest rate of dust applied was 1.2 cc/disk [14.2 cc/929 $cm^2$; that rate was successively halved and tested to the lowest rate of 0.06 cc/929 $cm^2$ (i.e., 9 rates tested)]. For exposure on each treatment rate, fleas from eclosion jars were directed onto the carpet, where they were confined for 24 hours. One or two replicates of 12 to 20 fleas were used for most rates, but 3 replicates were used for some rates. Because fleas cannot climb on the plastic or jump high enough to escape, they remained in contact with the carpet at the bottom of the cylinder. Untreated disks served as controls. Tests were conducted under ambient laboratory conditions (approximately 74° F. and 45% RH) and in an incubator cabinet at 98% RH.

The efficacy of the dust treatments was determined from the percentage of fleas that died within a 24-hour exposure period. Live and dead fleas on each disk were counted after tapping all the fleas from a disk into a basin of cool water. Live fleas move and swim vigorously. Fleas were considered dead if they sank, were immobile, or if they only had feeble, barely perceptible movement of their appendages.

Effect of humidity and volatility. The specific application rate of 1.8 cc/929 $cm^2$ was used to compare the activity and volatility of the "active ingredient" in the present insecticide dust and some other dusts at ambient and 98% RH. Using the method described above, mortality at 24 hours was determined for fleas exposed to fresh insecticide, insecticide baked 48 hours at 250° F., diatomaceous earth, and silica aerogel. It was presumed that high temperature might drive off volatile actives, and that abrasive diatomaceous earth or sorptive non-fluorinated silica gel would provide greater kill at low humidity than at high humidity. Differences between rates of kill may indicate the mode of action of the insecticide dust.

Tests With Argentine Ants

Based on the results obtained with the present insecticide in tests against cockroaches and fleas, Argentine ants were exposed to selected low doses of the dust as well as to comparative doses of SG-68 desiccant. Worker ants collected from a citrus grove were aspirated for study approximately 30 minutes before the test began. Aliquots of ants (11–15 for each of three replicates per treatment) were dumped onto lightweight deposits of the present insecticide dust and SG-68 spread evenly over the surface of filter paper waxed into the floor of 9-cm diameter glass petri dishes. Knockdown of the ants was observed every 5 minutes until all the ants in the treatments were down. An untreated set of papers served as a control series. The exposure tests provided an indication of the relative speed of action of the present insecticide and the SG-68 dusts against this species.

Results And Discussion

An embodiment of the present invention mixes an alkaline earth metal carbonate, such as calcium carbonate, an alkali metal bicarbonate, such as sodium bicarbonate, at least one neurally effective substance, and an absorbent material, such as diatomaceous earth. In addition, inert ingredients such as silica gel and a scenting agent may be added as desired in varying amounts for color and texture. Aside from the scenting agent, all of the above-mentioned ingredients are preferably mixed in powdered form.

The relative concentrations of the mixture are preferably about 30%–35% alkaline earth carbonate, 60%–65% alkali metal carbonate, 1%–2% neurally effective substance, and 4$–5% absorbent material (all by weight). However, the individual constituents may vary within the following ranges while still achieving the desired result: 5%–91% alkaline earth carbonate, 6%–95% alkali metal carbonate, 1%–93% neurally effective, and up to 90% absorbent material (all by weight). The mix is ground to a powder, preferably having a granular size of less than 100 microns.

The irreversible knockdown (KD) of cockroaches exposed to fresh and aged deposits of this embodiment the present insecticide at moderate and high humidities is summarized in Table 1.

52% of the cockroaches being alive at 7 days and 40% alive at 14 days. Boric acid dust, on the other hand, provided 98% kill of cockroaches within a week.

Table 2 also shows that a high percentage of the live cockroaches in choice boxes treated with the present insecticide were always in the less-preferred light compartment, away from the dust. This was not so with boric acid, a non-repellent insecticide. Avoidance of the dust by survivors is characteristic of repellent insecticides such as silica gels (repellent by nature of their small particle size and sorptive properties) and fast-knockdown toxicants such as pyrethrins and pyrethroids.

TABLE 1

Knockdown of adult male German cockroaches confined to dust deposits aged and tested at high (98%) and moderate (58%) humidity

| | | Avg. hours for KD on deposits of indicated age | | | | | |
|---|---|---|---|---|---|---|---|
| | | Fresh | | 2 Weeks | | 4 Weeks | |
| Treatment[a] | RH | KT-50 | KT-90 | KT-50 | KT-90 | KT-50 | KD-90 |
| Present insecticide | 58% | 0.3 | 0.6 | 0.3 | 0.7 | 0.3 | 0.7 |
| Silica gel | | 6.1 | 16.0 | 4.3 | 5.8 | 7.4 | 18.4 |
| Celite | | (39%)[b] | | (6%) | | (42%) | |
| Untreated | | (0%) | | (0%) | | (16%) | |
| Present insecticide | 98% | 0.3 | 0.5 | 0.6 | 1.2 | 0.7 | 1.3 |
| Silica gel | | 6.7 | 12.3 | 8.3 | 17.3 | 13.3 | 21.9 |
| Celite | | (4%) | | (0%) | | (16%) | |
| Untreated | | (0%) | | (0%) | | (13%) | |

[a]1 cc/9-cm-diam petri dish. Five replicates each with 10 cockroaches, were used for each exposure. Dusts spread onto Whatman No. 1 filter paper. Silica gel was SG-68 silica aerogel, an aerogel containing no fluoride. Celite is a commercial diatomaceous earth filter aid (Manville, Hyflo ™).
[b]Numbers in parentheses indicate total % KD at 24 hours, in instances where average KT-50 was not achieved.

The present insecticide dust provided rapid KD of German cockroaches, the average KT-50 being about 18 minutes, and 100% being down within about 40 minutes. Neither high humidity nor aging up to 4 weeks had a deleterious effect on its speed of action against cockroaches. Because even the most rapid-action desiccants require >30 minutes for KD, the effect observed with present insecticide suggests that the toxic action of the dust was not attributable solely to a sorptive ingredient. The affected cockroaches had curled or distended abdomens, and looked to be paralyzed as when toxified by a nervous system insecticide.

As expected, the non-fluorinated SG-68 desiccant took several hours to kill cockroaches, and was slightly less effective at high humidity. Typically, the desiccated cockroaches died standing upright, and did not show signs of tremors or paralysis.

Diatomaceous earth (like Celite™) alone is not usually considered to be an effective insecticide. Being an abrasive, the toxic action of diatomaceous earth occurs as a result of dusted insects slowly losing body water through abraded cuticle. Because moist air has little evaporative power, Celite ™ was even less effective at high humidity.

Choice box tests with cockroaches. Although the present insecticide dust provided rapid kill in continuous exposure tests, there was significant survivorship in the choice tests. There is usually a direct relationship between the speed of action of an insecticide and its repellency, and this relationship appears to have been confirmed in the choice box study. As shown in Table 5, deposits of the present insecticide dust provided mediocre kill of cockroaches in choice boxes, with

TABLE 2

Activity and repellency of fresh dust deposits against German cockroaches, as measured in choice boxes

| | % Mortality on day | | | % of live in light on day | | | Days for KD[b] | |
|---|---|---|---|---|---|---|---|---|
| Dust[a] | 1 | 7 | 14 | 1 | 7 | 14 | KT-50 | KT-90 |
| Present insecticide | 25 | 48 | 60 | 84 | 100 | 100 | 7.7 | — |
| Boric acid, tech. | 0 | 98 | 100 | 13 | 100 | — | 4.0 | 5.7 |
| Untreated | 0 | 3 | 10 | 12 | 3 | 18 | — | — |

[a]10 cc dust spread evenly over floor of dark compartment. For each dust, 3 replicates were tested, each with 20 adult male B. germanica.
[b]KT-50 and KT-90 are average days for 50% and 90% of the cockroaches to be irreversibly knocked down (KD).

The present insecticide dust, therefore, had high intrinsic insecticidal action against cockroaches, it had excellent activity at high and low humidity, and it retained activity for at least a month. The dust was, however, somewhat repellent, resulting in a high percentage of cockroaches surviving in choice tests. Direct application to cockroaches would certainly kill them.

Speed of action and minimum effective dose against fleas. A low dose of the present insecticide dust provided very rapid knockdown of adult fleas. On paper in tubes it took nearly 4 hours for 90% knockdown of fleas on SG-68 silica gel, but less than 5 minutes for knockdown on the present insecticide. As with cockroaches, this rapid action suggests the presence of a nerve-involving insecticide rather than an adsorptive desiccant or an abrasive.

The good activity against fleas at a low dose was substantiated in the series of exposure tests with successively lower doses of the present insecticide on carpet. As shown in Table 3, complete kill of fleas was achieved with as little as 0.2 cc/929 cm$^2$ of the present invention. Lower doses were not effective.

TABLE 3

Minimum effective dosages of fresh dust deposits on carpet against adult cat fleas, *Cunocephalides felis*

| | % Mortality of fleas at 24 hours[a] | | | |
|---|---|---|---|---|
| Rate | Present insecticide | | Silica gel (SG-68) | |
| (cc/929 cm$^2$)[b] | Ambient RH | 98% RH | Ambient RH | 98% RH |
| 14.2 | 100 | 100 | 100 | 100 |
| 7.1 | 100 | 100 | 100 | 100 |
| 3.6 | 100 | 100 | 100 | 100 |
| 1.8 | 100 | 93.6 | 100 | 92.3 |
| 0.9 | 100 | 100 | 100 | 100 |
| 0.4 | 100 | 77.8 | 100 | 42.9 |
| 0.2 | 100 | 81.8 | 100 | 46.7 |
| 0.1 | 23.5 | — | 100 | — |

TABLE 3-continued

Minimum effective dosages of fresh dust deposits on carpet against adult cat fleas, *Cunocephalides felis*

| | % Mortality of fleas at 24 hours[a] | | | |
|---|---|---|---|---|
| Rate | Present insecticide | | Silica gel (SG-68) | |
| (cc/929 cm$^2$)[b] | Ambient RH | 98% RH | Ambient RH | 98% RH |
| 0.06 | 4.1 | — | 1.8 | — |
| Untreated | 9.7 | 11.3 | — | — |

[a]% mortality of treatments corrected with Abbott's formula to account for control mortality.
[b]Rates extrapolated from volume amounts applied to 78.5 cm$^2$ carpet discs. Highest rate applied (14.2 cc/929 cm$^2$) is equivalent to 1.2 cc/disc; other rates are proportional.

High humidity appeared to reduce the effectiveness of the dust at low rates of application as shown in Table 4.

TABLE 4

Effect of humidity on the activity of a low dose of dust deposit against adult cat fleas

| | % Mortality at indicated RH[a] | |
|---|---|---|
| Dust treatment | Ambient | 98% |
| Present insecticide | 100 | 93.6 |
| Present insecticide (baked)[b] | 72.7 | 2.8 |
| Celite | 21.4 | 23.1 |
| Silica gel | 100 | 92.3 |
| Untreated | 5.6 | 6.4 |

[a]Fresh powders (1.8 cc/929 cm$^2$) applied to carpet. Fifteen to 20 fleas confined to treatments 24 hours. One to 2 replicates per treatment. Ambient humidity 25–40% RH.
[b]Heated 48 hours in hot-air oven at 250° F.

Surprisingly, the SG-68 also provided good kill at approximately the same low rates. Since SG-68 is a non-toxic desiccant, it could have been concluded erroneously that the present insecticide dust also killed fleas by desiccating them. The much more rapid action found in the test tube assay suggests that there is a toxic component in the present insecticide formulation. The toxic component appears to involve toxification of the insect's nerves or cells.

Activity of the present insecticide against Argentine ants. The rapid activity of the present insecticide against Argentine ants is shown in Table 5.

TABLE 5

Activity of minimal dust deposits against the Argentine ant, *Iridomyrmex humilis*

| Dust | Rate (cc/929 cm$^2$) | % Dead at minutes of exposure | | | | | | Time for KD (min) | |
|---|---|---|---|---|---|---|---|---|---|
| | | 5 | 10 | 20 | 40 | 60 | 80 | KT-50 | KT-90 |
| Present Insecticide | 0.2 | 36 | 100 | | | | | 6.0 | 9.2 |
| | <0.06 | 23 | 32 | 100 | | | | 11.2 | 14.2 |
| SG-68 | 0.2 | 0 | 0 | 0 | 23 | 66 | 89 | 55.9 | 75.7 |
| | <0.06 | 0 | 0 | 0 | 24 | 84 | 100 | 49.5 | 60.3 |
| Untreated | — | 0 | 0 | 0 | 0 | 7 | 7 | — | — |

[a]Mortality based on 3 replicates, each with 11–15 worker ants.

The lightweight deposit (0.2 cc/929 cm$^2$) knocked down all the ants in less than 10 minutes; and an extremely light deposit (<0.06 cc/929 cm$^2$) provided effects that were nearly as rapid. The latter deposit was achieved by brushing a small amount of the dust onto the paper, and then tapping the remnant dust off the paper as the dish was inverted. Only a very small amount of dust remained. The SG-68 desiccant had a somewhat slower effect, resulting in high levels of KD within about 50 to 75 minutes. Desiccants such as SG-68 are active against ants such as these, perhaps because this ant has a relatively low percentage body water (<70%) and a large surface area compared to its body volume, a combination of which allows for rapid water loss from this insect.

As with the exposures of cockroaches and fleas, the ants contacting the present insecticide dust exhibited classic symptoms of neural toxication. Ants contacting the dust were quickly paralyzed. There was rapid running and apparent irritation before the onset of paralysis, a symptom often observed with ants exposed to finely divided dusts and fast-acting insecticides. There appeared to be less irritation among ants exposed to SG-68.

As with all dust formulations, care should be exercised to minimize airborne particulates of the dust at the time of application or afterwards. This may be more important if the dust is applied to carpet or furnishings for controlling fleas than if applied along baseboards, under appliances, or in other similar places for controlling cockroaches or ants.

The presence of a volatile active component in the present insecticide formulation was preliminarily verified when the activity of fresh insecticide was compared to that of heated (i.e., baked) insecticide. As shown in Table 4, the present insecticide baked 48 hours at 250° F. was less effective against fleas, and was significantly less effective when tested at high humidity. Baking apparently removed volatile active components or altered the configuration of the dust diluent. That removal or alteration reduced activity. Baking at higher temperature may reduce performance even more. Pyrethins and other botanical insecticides volatilize at 250° F., but can reportedly be more quickly and thoroughly removed at 350° F.

The effectiveness compares favorably to conventional pesticides, yet the above-described product is primarily inorganic and completely non-hazardous to humans and other animals.

An improved embodiment of the present invention using the neurally effective substances with the inorganic dust was prepared and tested as described below.

A control test was conducted using only the solid components of the embodiment. As summarized in Table 6, the least active dust substance was calcium carbonate, ($CaCO_3$). Only 10% of the cockroaches exposed to deposits of $CaCO_3$ were KD within 24 hours. The activity of $CaCO_3$ was not statistically different from the untreated control, and was the most inert of the ingredients tested. Amorphous silica (HiSil (R)233 marketed by Harwick, Akron, Ohio has been used satisfactorily), on the other hand, is a potent desiccant and was the most active of the dry ingredients, it's average $KT_{90}$ being 6.7 hours. The addition of amorphous silica to $CaCO_3$ proportionately increased the activity of the $CaCO_3$ obviously because of the sorptive qualities of the amorphous silica. As expected, diatomaceous earth and sodium bicarbonate were not highly insecticidal but they did provide significant KD within 24 hours. These data suggested that calcium carbonate was a suitable inert ingredient with which to determine the relative effects attributable to the neurally effective substances. $CaCO_3$ was used as an inert carrier or diluent in further tests to determine mechanisms of insecticidal action as described hereinafter.

TABLE 6

Average hours (± standard deviation) for 50% and 90% knockdown of adult male German cockroaches, Blattella, germanica, continuously confined to dust deposits.

| Dust or dust mix | $KT_{50}$ | | $KT_{90}$ | |
| --- | --- | --- | --- | --- |
| | Hours | ±SD | Hours | ±SD |
| Calcium carbonate ($CaCO_3$) | — | — | (10% KD at 24 h) | |
| Amorphous silica (AS) | 4.9 | 0.38 | 6.7 | 1.38 |
| Diatomaceous Earth (DE) | 11.8 | 1.44 | 16.8 | 3.03 |
| Sodium bicarbonate ($NaHCO_3$) | 16.5 | 0.48 | 20.9 | 0.10 |
| $CaCO_3$ + 30% AS | 6.5 | 1.00 | 9.3 | 1.53 |
| $CaCO_3$ + 30% AS + 5% DE | 6.3 | 1.19 | 10.8 | 3.70 |
| $CaCO_3$ + 36% $NaHCO_3$ | 19.5 | 0.50 | (80% KD at 24 h) | |
| $CaCO_3$ + 5% AS | 13.7 | 3.44 | 19.4 | 1.52 |
| Untreated control | — | — | (0% KD at 24 h) | |

Average values based on 3 replicates, each with 10 cockroaches. SD = standard deviation. Exposures at 76° F., 55% relative humidity.

The pesticidal activity of the neurally effective substances combined only with $CaCO_3$ was determined. Each respective neurally effective substance was formulated at 5% (wt/wt) in $CaCO_3$ and cockroaches were confined to the mixture as described above for exposures to the dry dust ingredients. Weighed quantities of compound were added to $CaCO_3$ and the mix was thoroughly stirred in 500 ml glass beakers and then shaken with glass boiling beads in a capped specimen jar. The beads were screened out of the resultant mix. Exactly 1.2 cc of dust or dust was spread onto Whatman filter paper in 9-cm-diam petri dishes and the knockdown (KD) of cockroaches confined to the dust mix was determined by periodically observing KD.

The insecticidal activity of the neurally effective substances is summarized in Table 7. Again, $CaCO_3$ was not insecticidal and both sodium bicarbonate and diatomaceous earth provided comparatively slow KD. The most active neurally effective substances were benzyl acetate, phenyl ethyl alcohol, and terpineol. Each of these substances provided 90% KD of cockroaches in about one hour or so. Amyl cinnamic aldehyde was much slower, about as active as diatomaceous earth. Diethyl phthalate and dipropylene glycol may impart some favorable odor characteristics but they were not insecticidal. The complete dust embodiment of the present invention as described herein provided fastest KD, the $KT_{90}$ for it being only about 0.5 hours.

TABLE 7

Average hours (± standard deviation) for 50% and 90% knockdown of German cockroaches continuously confined to calcium carbonate + 5% ingredients of neurally effective substance.

| Dust or dust mix | $KT_{50}$ | | $KT_{90}$ | |
| --- | --- | --- | --- | --- |
| | Hours | ±SD | Hours | ±SD |
| Calcium carbonate (dust) | — | — | (1.3% KD at 24 h) | |
| Sodium bicarbonate (dust) | 9.7 | 0.48 | 16.0 | 1.88 |
| Diatomaceous Earth (dust) | 9.4 | 0.00 | 15.5 | 0.00 |
| Amyl cinnamic aldehyde, 5% | 9.4 | 0.00 | 15.5 | 0.00 |
| Benzyl acetate | 0.7 | 0.05 | 1.0 | 0.18 |
| Diethyl phthalate | — | — | (0% KD at 18 h) | |
| Phenyl ethyl alcohol | 0.7 | 0.09 | 1.0 | 0.25 |
| Dipropylene glycol | — | — | (23% KD at 18 h) | |
| Terpineol | 0.7 | 0.08 | 1.1 | 0.17 |
| Dust embodiment* | 0.2 | 0.06 | 0.5 | 0.03 |

Average values based on 3 replicates, each with 10 cockroaches. SD = standard deviation. Exposures in laboratory at 78 ± 4° F., 55 ± 6% rh.
*The dust embodiment of the present invention contains benzyl acetate, terpineol and phenyl ethyl alcohol.

The above exposure trials with cockroaches indicate that the rapid pesticidal action of the formulation of the present invention is due to the neurally effective substance, not to any of the powdered components, either individually or combined.

A further test was conducted to compare the effectiveness of phenol vs. terpineol as a neurally effective substance. The respective substances were mixed with calcium carbonate at a range of wt/wt mixes. The preparations were tested using German cockroaches with the results provided in Table 8.

TABLE 8

Average hours for 50% and 90% knockdown of German cockroaches continuously confined to calcium carbonate + ingredients of phenol and terpineol

| Dust | % (wt/wt) | KT-50 (h) | KT-90 (h) |
| --- | --- | --- | --- |
| Phenol | 5.0 | <0.1 | 0.1 |
| | 2.5 | 0.2 | 0.4 |
| | 1.25 | 0.4 | 1.5 |
| | 0.63 | 7.5 | 20.3 |

TABLE 8-continued

Average hours for 50% and 90% knockdown of German
cockroaches continuously confined to calcium carbonate +
ingredients of phenol and terpineol

| Dust | % (wt/wt) | KT-50 (h) | KT-90 (h) |
|---|---|---|---|
|  | 0.32 | 16.5 | 24.0 |
| Terpineol | 5.0 | 0.6 | 0.9 |
|  | 2.5 | 9.4 | 20.6 |
|  | 1.25 | 11.4 | 23.5 |
|  | 0.63 | 14.7 | 22.1 |

Phenol was more insecticidal than terpineol. It is also much more toxic to humans and other mammals than are the other neurally effective substances tested. Cockroaches killed in the phenol mix turned black. At every rate tested, phenol provided faster KD. The minimum active dose for fresh phenol in $CaCO_3$ was approximately between 1.25% and 0.63%. The minimum active dose for fresh terpineol was above 2.5%. This assay confirms the theory as discussed below that speed of insecticidal activity of the neurally effective substances may be associated with the complexity and isomeric configuration of hydroxyl attachments to a six member carbon ring.

Having now fully set forth a detailed example and certain modifications incorporating the concept underlying the present invention, various other modifications will obviously occur to those skilled in the art upon becoming familiar with said underlying concept. It is to be understood, therefore, that within the scope of the appended claims, the invention may be practiced otherwise than as specifically set forth herein.

The mode of action of the neurally effective substances disclosed herein is not known. Each of the substances is considered to be non-toxic by the U.S. Food and Drug Administration and are frequently used in food and food additives. The applicants are unaware of pesticidal activity reported or ascribed to the neurally effective compounds as specifically taught herein.

It is proposed that in biology, the body's receptacles have an affinity for hydroxyl compounds, and are absorbed into the nerve endings, creating a genomic effect, which is highly desirable in a mode of action context. The more distal from the six member carbon ring that the hydroxyl is, the less likely it is that the body can metabolize this compound to the point that the hydroxyl can attach itself to the receptacle. Separation of the hydroxyl group from the ring by a chain of up to four (4) carbon atoms results in a corresponding decrease in activity. In general, carbon chains of five (5) or greater are usually inactive.

There is credible evidence that this in fact takes place, based on theories that estrogen and other pharmeuticals work in this manner. It is further postulated that the esters such as benzyl acetate are active because the body hydrolyzes the ester, enabling the hydroxyl group to become available for interaction with the body's receptacles. However, applicants do not wish to be bound by any specific theory of operation.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A method of controlling adult ants, adult cockroaches and adult fleas comprising applying to the adult ants, adult cockroaches and adult fleas, an effective amount of a contact pesticide to kill adult ants, adult cockroaches and adult fleas, the contact pesticide comprising a neurally effective substance dispersed in a carrier, the neurally effective substance being benzyl acetate.

2. A method of controlling adult ants, adult cockroaches and adult fleas comprising applying to the adult ants, adult cockroaches and adult fleas, an effective amount of a contact pesticide to kill adult ants, adult cockroaches and adult fleas, the contact pesticide comprising a neurally effective substance dispersed in a carrier, the neurally effective substance being eugenol.

3. A method of controlling adult ants, adult cockroaches and adult fleas comprising applying to the adult ants, adult cockroaches and adult fleas, an effective amount of a contact pesticide to kill adult ants, adult cockroaches and adult fleas, the contact pesticide comprising a neurally effective substance dispersed in a carrier, the neurally effective substance being phenyl ethyl alcohol.

4. A method of controlling adult ants, adult cockroaches and adult fleas comprising applying to the adult ants, adult cockroaches and adult fleas, an effective amount of a contact pesticide to kill adult ants, adult cockroaches and adult fleas, the contact pesticide being a neurally effective substance dispersed in a carrier, wherein the neurally effective substance is selected from the group consisting of benzyl acetate, eugenol and phenyl ethyl alcohol and mixtures thereof.

5. The method of claim 4 wherein the neutrally effective substance is approximately 0.01% to 10% by weight of the pesticide.

* * * * *